United States Patent [19]
Hagelauer

[11] Patent Number: 5,383,455
[45] Date of Patent: Jan. 24, 1995

[54] APPARATUS FOR THE GENERATION OF FOCUSSED ACOUSTIC PRESSURE OR SHOCK WAVES FOR THERAPEUTICAL APPLICATIONS WITH AN X-RAY LOCATING DEVICE

[75] Inventor: Ulrich Hagelauer, Bottighofen, Germany

[73] Assignee: Storz Medical AG, Kreuzlingen, Germany

[21] Appl. No.: 952,706

[22] PCT Filed: Mar. 24, 1992

[86] PCT No.: PCT/EP92/00651
§ 371 Date: Jan. 22, 1992
§ 102(e) Date: Jan. 22, 1992

[87] PCT Pub. No.: WO92/17119
PCT Pub. Date: Oct. 15, 1992

[30] Foreign Application Priority Data
Mar. 24, 1991 [DE] Germany ............... 4109558

[51] Int. Cl.⁶ .............. A61B 6/00; A61B 17/22
[52] U.S. Cl. .................... 128/653.1; 601/4; 378/162; 378/205
[58] Field of Search .......... 128/24 AA, 24 EL, 653.1; 378/162, 205; 601/2-4

[56] References Cited
U.S. PATENT DOCUMENTS
5,070,861 12/1991 Einars et al. ............... 128/24 EL Primary Examiner—Ruth S. Smith
Attorney, Agent, or Firm—Antonelli, Terry, Stout & Kraus

[57] ABSTRACT

An apparatus for destroying a concretion in a patient with focussed pressure waves includes a pressure wave source for generating focussed pressure waves focussed at a pressure wave focal point for destroying a concretion in a patient, an X-ray source for emitting X-rays, an X-ray receiver for receiving the X-rays from the X-ray source, and an aiming device for enabling the concentration to be positioned at the pressure wave focal point. The aiming device is disposed in an X-ray path between the X-ray source and the X-ray receiver for projecting a pattern on the X-ray receiver when the X-ray source emits X-rays. The aiming device has a structure such that the pattern projected on the X-ray receiver is independent of a location of the X-ray source and the X-ray receiver, and such that a line connecting the X-ray source and a center of the pattern projected on the X-ray receiver always extends through a fixed point in space outside the aiming device, the fixed point in space outside the aiming device being located at a predetermined position relative to the pressure wave focal point.

30 Claims, 3 Drawing Sheets

APPARATUS FOR THE GENERATION OF FOCUSSED ACOUSTIC PRESSURE OR SHOCK WAVES FOR THERAPEUTICAL APPLICATIONS WITH AN X-RAY LOCATING DEVICE

TECHNICAL FIELD

The present invention relates to an apparatus for the generation of focussed acoustic pressure or shock waves for therapeutical applications and, in particular, for the destruction of concretions, calculi, etc., having a pressure or shock wave source, a locating device for the concretion to be destroyed provided with an X-ray machine having an aiming device, which can be projected by means of an X-ray beam from the X-ray source onto the X-ray receiver, and a patient support.

Apparatuses for the generation of focussed acoustic pressure or shock waves for therapeutical applications and, in particular, for the destruction of concretions, calculi, etc., for the acoustic radiation of body tissue in living creatures require aiming or locating devices in order to position the concretion or tissue in the focus of the pressure wave source.

STATE OF THE ART

In known apparatuses, one or several X-ray axes, which are attached in a fixed spatial arrangement at the apparatus are employed for aiming. A hairline cross on the monitor marks the intended point of penetration of a straight line from the X-ray source through the shock wave focus and through the reception plane. For localization, two X-ray pictures with different solid angles are required with the point of intersection of both straight lines having to run through the focal point or region of the acoustic waves. Both the penetrating radiation directions may be realized by two X-ray axes; as an alternative an X-ray axis may be moved mechanically in such a manner that the described straight line always runs through the focal point. For aiming precision, depending on the size of the focal point or region, a deviation of less than 1-2 mm is required. If this condition is not fulfilled, a health risk to the patient arises because the tissue next to the concretion will be hit. For this reason, a relatively technically highly complex construction is needed in order to achieve the necessary precision of movement.

Furthermore, aiming devices imaged in conjunction with the area of interest of the body on the reception surface are known from DE 39 19 083 A1. However, these aiming devices have the problem that the X-ray machine has to either be moved very precisely (fore and backsight in line with the focal point of the X-ray tube) or, if a spatial deviation of the focal point is admissible, a complex reconstruction of the focal point from the projected figures is necessary. Described are light pens with which the physician has to mark the figures on the monitor and a computer evaluation unit connected thereafter.

Thus the known aiming device is not only more time consuming for the physician, but also requires a relatively technically highly complex construction.

DESCRIPTION OF THE INVENTION

The object of the present invention is to further improve an apparatus for the generation of focussed acoustic pressure or shock waves for therapeutical applications having an X-ray locating device in such a manner that technical complexities and time consumption are distinctly reduced compared to the state of the art without detriment to locating precision and, in particular, that the received X-ray pictures can be visually evaluated.

In one solution in accordance with the present invention, the apparatus is improved by designing the aiming device in such a manner that its projection onto the X-ray receiver is a figure which is independent of the location of the X-ray source and the X-ray receiver, and a line connecting the X-ray source and the center of the projected figure always runs through a point fixed in space outside the aiming device.

The present invention is made more apparent in the following section by way of example without the intention of limiting the scope or spirit of the overall inventive idea using embodiments with reference to the accompanying drawing, to which is to be referred for the disclosure of any invented details not explained more closely herein.

DESCRIPTION OF EMBODIMENTS

In the following figures, the same or corresponding elements are denoted with the same letter making repeated explanation unnecessary and only the deviations of the embodiments illustrated in these figures from the first embodiment are explained.

Figure 1:
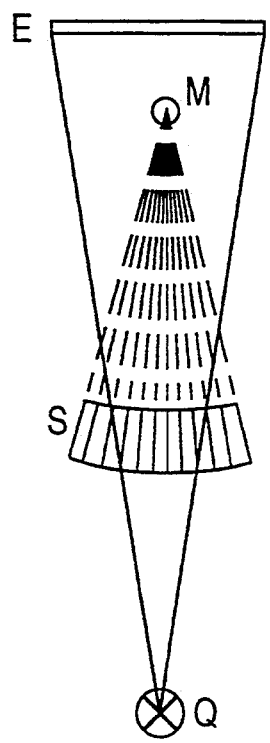
FIG. 1 shows an illustration of the fundamental concept of the invention.
Figure 2:
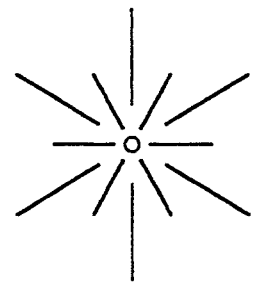
FIG. 2 shows a diagram of the resulting X-ray picture.

FIG. 1 explains the fundamental concept of the invention. In a spherical section S of a hollow sphere are either channels, if the material of the spherical section S absorbs the radiation from an X-ray source Q, or pins, if the material of the spherical section S is transparent to the X-rays. In any event, the channels or the pins are aimed at the center M of the spherical section. If such a structure is projected by the X-ray source Q onto a reception surface E, a pattern of X-ray shadows or X-ray brightenings is the result, as illustrated in FIG. 2.

The essential features of the structure illustrated by way of example of spherical section S in FIG. 1 are that independent of the location of the X-ray source Q and the reception surface E, similar patterns are always produced, and a line connecting the X-ray source and the center of the projected pattern always runs through the center M of the spherical section S. The technical complexity of the precise positioning of the X-ray source and the X-ray receiver is thus eliminated. A further advantage can be that the figure is evaluated solely visually because the eye can recognize the center of the pattern as being the center. The process therefore exploits the ability peculiar to human vision of recognizing patterns and utilizes it to replace technical image-processing means.

Figure 3:
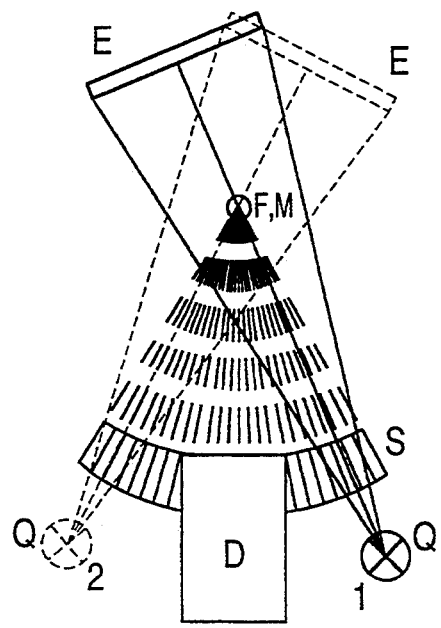
FIG. 3 shows a section of an apparatus designed according to the present invention.

FIG. 3 depicts the arrangement of the structure illustrated in Fig. 1 at a pressure wave source D, with the focal point F of the pressure wave source D and the center M of the spherical section S at which the spherical section S is aimed concurring.

In a first position 1 of the X-ray source, a concretion not lying in the focus is X-rayed in conjunction with the spherical section S and imaged onto the reception surface E. The patient is then moved in such a manner that the shadow of the concretion lies in the center (FIG. 2) of the projected pattern.

This moving occurs in a plane which is parallel to the reception surface E. The process is repeated in a second position 2 of the X-ray source, with the moving occurring this time perpendicular to the reception surface E. Following these two steps, the concretion is located at the center M of the spherical section S which is also the focal point of the pressure wave source D.

Figure 4:
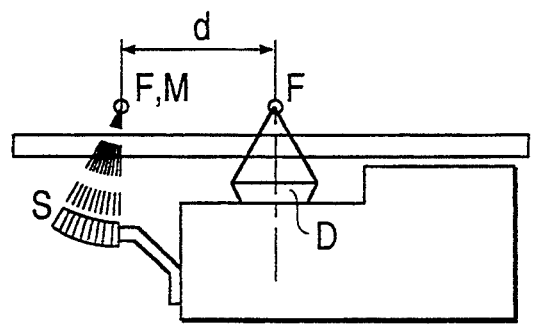
FIG. 4 shows an apparatus designed according to the present invention having a patient support.

FIG. 4 depicts an inventive device having a patient support constituted by a moveable table, such as a moveable cot, as described in DE 38 35 317A1. Such a lithotripter permits moving the cot of the patient in a longitudinal direction between two defined points. The positioning of the concretion occurs at a virtual focal point F', which is located at a defined distance d from the focal point F of the pressure wave source D. The locating structure is attached to the basic apparatus in such a manner that the center M of the spherical section S concurs with the point F'. The positioning of the concretion occurs as described above, with the patient being moved toward F following positioning at F'. In order to take control pictures without the superimposed location structure, the latter may be shifted, swung or the like to the side out of the beam path of the X-ray machine.

FIGS. 5 to 8 depict various embodiments of locating structures, or aiming devices having the mentioned features, i.e. which are, designed in such a manner that their projection onto the X-ray receiver is a figure which is independent of the location of the X-ray source and the X-ray receiver and that a line connectingly the X-ray source and the center of the projected figure always runs through a fixed point in space outside the aiming device.

Figure 5:
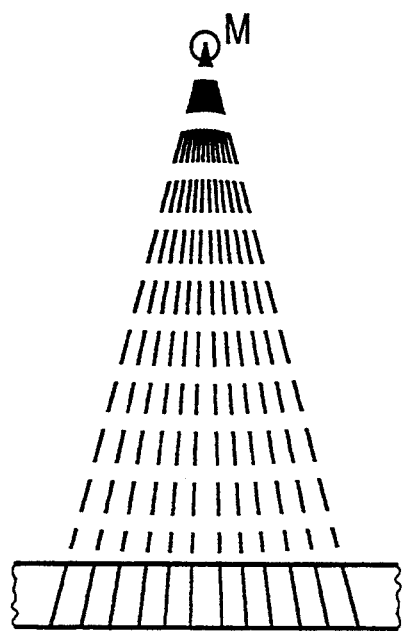
FIGS. 5 to 11 show various embodiments of the invented aiming device.
Figure 6:
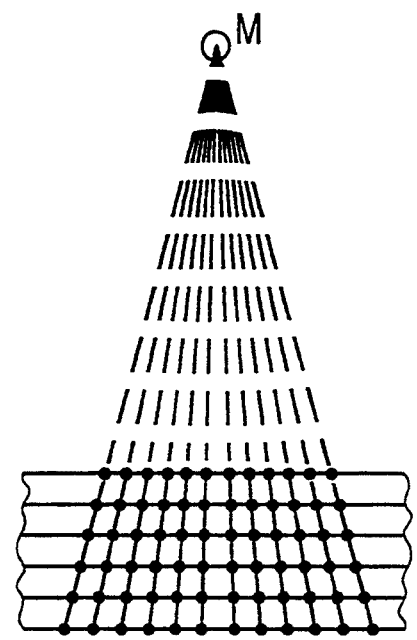
Figure 7:
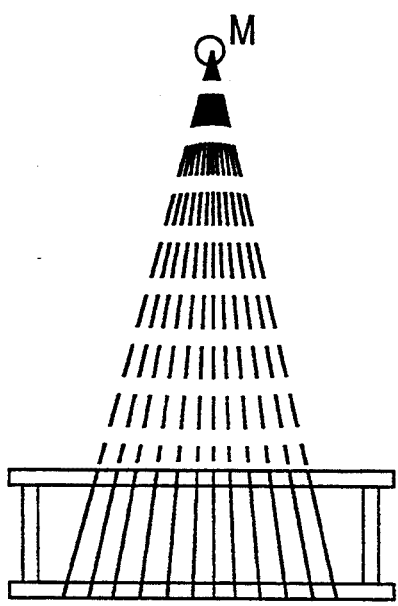
Figure 8:
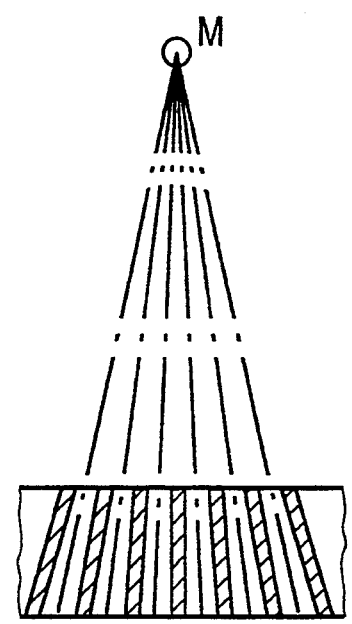
Figure 9:
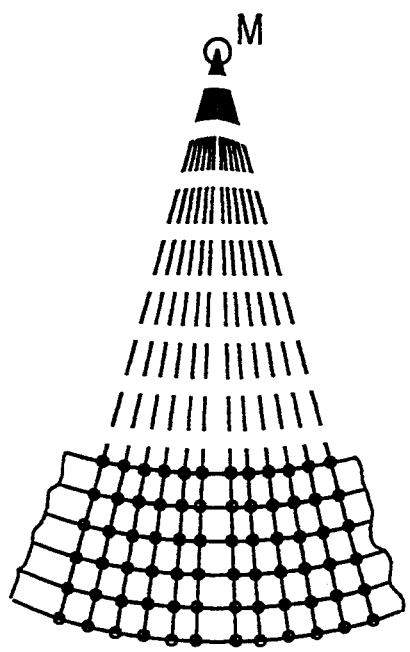
Figure 10:
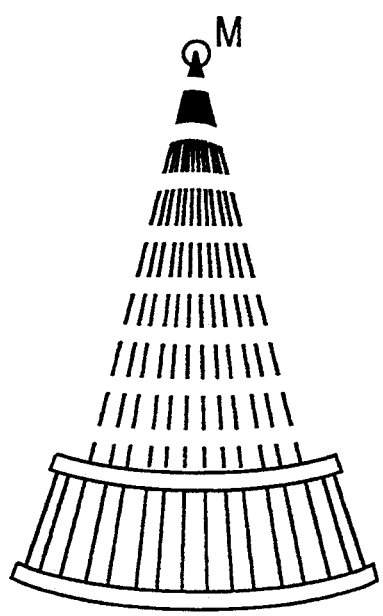
Figure 11:
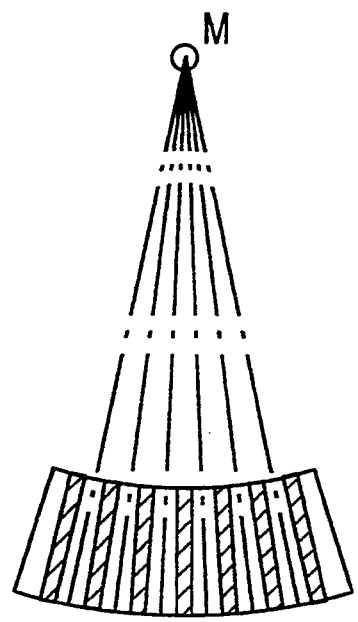

FIG. 5 depicts a plane plate in which channels, pins or wires are placed aiming at a point M.

What is claimed is:

1. An apparatus for destroying a concretion in a patient with focussed pressure waves, the apparatus comprising:
    a pressure wave source for generating focussed pressure waves focussed at a pressure wave focal point for destroying a concretion in a patient;
    an X-ray source for emitting X-rays;
    an X-ray receiver for receiving the X-rays from the X-ray source; and
    an aiming device for enabling the concretion to be positioned at the pressure wave focal point, the aiming device being disposed in an X-ray path between the X-ray source and the X-ray receiver for projecting a pattern on the X-ray receiver when the X-ray source emits X-rays, the aiming device having a structure such that the pattern projected on the X-ray receiver is independent of a location of the X-ray source and the X-ray receiver, and such that a line connecting the X-ray source and a center of the pattern projected on the X-ray receiver always extends through a fixed point in space outside the aiming device, the fixed point in space outside the aiming device being located at a predetermined position relative to the pressure wave focal point.

2. An apparatus according to claim 1, further comprising means for moving the X-ray source and the X-ray receiver relative to the aiming device to at least two different positions relative to the aiming device, thereby enabling the pattern to be projected on the X-ray receiver at the at least two different positions of the X-ray source and the X-ray receiver relative to the aiming device, thereby providing at least two different pattern projection directions.

3. An apparatus according to claim 1, wherein the fixed point in space outside the aiming device coincides with the pressure wave focal point.

4. An apparatus according to claim 1, wherein the fixed point in space outside the aiming device is located a predetermined distance from the pressure wave focal point, and wherein the apparatus further comprises means for moving the patient between a first position at which the concretion is located at the fixed point in space outside the aiming device and a second position at which the concretion is located at the pressure wave focal point.

5. An apparatus according to claim 1, wherein the aiming device includes a plate and structures in the plate, the structures defining the pattern and being aimed at the fixed point in space outside the aiming device, the plate and the structures having mutually different X-ray transmission characteristics.

6. An apparatus according to claim 5, wherein the plate is a plane plate.

7. An apparatus according to claim 5, wherein the plate is a curved plate.

8. An apparatus according to claim 7, wherein the curved plate is a spherical section of a hollow sphere, the hollow sphere having a center coinciding with the fixed point in space outside the aiming device.

9. An apparatus according to claim 5, wherein the plate absorbs X-rays and the structures are transparent to X-rays.

10. An apparatus according to claim 9, wherein the structures are channels in the plate.

11. An apparatus according to claim 5, wherein the plate is transparent to X-rays and the structures absorb X-rays.

12. An apparatus according to claim 1, wherein the structures are pins disposed in the plate.

13. An apparatus according to claim 1, wherein the aiming device includes two plates and structures disposed between the plates, the structures defining the pattern and being aimed at the fixed point in space outside the aiming device, the plates and the structures having mutually different X-ray transmission characteristics.

14. An apparatus according to claim 13, wherein the plates are plane plates.

15. An apparatus according to claim 13, wherein the plates are curved plates.

16. An apparatus according to claim 15, wherein each of the curved plates is a spherical section of a respective hollow sphere, the respective hollow sphere having a respective center coinciding with the fixed point in space outside the aiming device.

17. An apparatus according to claim 13, wherein the plates are transparent to X-rays and the structures absorb X-rays.

18. An apparatus according to claim 17, wherein the structures are pins.

19. An apparatus according to claim 1, wherein the aiming device includes a plurality of plates disposed one on top another to form a plurality of layers, and structures in surfaces of the plates, the structures being arranged such that the structures define lines defining the pattern, the lines defining the pattern being aimed at the fixed point in space outside the aiming device, the plates and the structures having mutually different X-ray transmission characteristics.

20. An apparatus according to claim 19, wherein the plates are plane plates.

21. An apparatus according to claim 19, wherein the plates are curved plates.

22. An apparatus according to claim 21, wherein each of the curved plates is a spherical section of a respective hollow sphere, the respective hollow sphere having a respective center coinciding with the fixed point in space outside the aiming device.

23. An apparatus according to claim 19, wherein the plates absorb X-rays and the structures are transparent to X-rays.

24. An apparatus according to claim 23, wherein the structures are voids in the surfaces of the plates.

25. An apparatus according to claim 19, wherein the plates are transparent to X-rays and the structures absorb X-rays.

26. An apparatus according to claim 25, wherein the structures are X-ray absorbing material disposed in the surfaces of the plates.

27. An apparatus according to claim 1, wherein the aiming device includes a plate with a honeycomb structure having chambers defining the pattern, the chambers defining the pattern being aimed at the fixed point in space outside the aiming device, the plate and the chambers having mutually different X-ray transmission characteristics.

28. An apparatus according to claim 27, wherein the plate is a plane plate.

29. An apparatus according to claim 27, wherein the plate is a curved plate.

30. An apparatus according to claim 29, wherein the curved plate is a spherical section of a hollow sphere, the hollow sphere having a center coinciding with the fixed point in space outside the aiming device.

* * * * *